United States Patent [19]
van Amerongen et al.

[11] Patent Number: 6,106,886
[45] Date of Patent: Aug. 22, 2000

[54] PROCESS FOR THE PRODUCTION OF STANOL ESTERS, AND USE THEREOF

[75] Inventors: Marnix P. van Amerongen, Vlaardingen, Netherlands; Lourus Cornelis Lievense, Valinhos, Brazil

[73] Assignee: Lipton, division of Conopco, Inc., Englewood Cliffs, N.J.

[21] Appl. No.: 09/135,722

[22] Filed: Aug. 18, 1998

[30] Foreign Application Priority Data

Aug. 22, 1997 [EP] European Pat. Off. .............. 97202597

[51] Int. Cl.[7] .................................................. A23D 9/007
[52] U.S. Cl. ........................................... 426/611; 552/554
[58] Field of Search .................... 426/601, 611; 552/554

[56] References Cited

U.S. PATENT DOCUMENTS

| | | | |
|---|---|---|---|
| 5,502,045 | 3/1996 | Miettinen | 514/182 |
| 5,892,068 | 4/1999 | Higgins | 552/554 |
| 5,929,062 | 7/1999 | Haines | 514/182 |
| 5,932,562 | 8/1999 | Ostlund | 514/78 |
| 5,958,913 | 9/1999 | Miettinen | 514/182 |
| 6,025,348 | 2/2000 | Goto | 514/182 |
| 6,031,118 | 2/2000 | van Amerongen | 426/603 |

FOREIGN PATENT DOCUMENTS

WO92/19640  11/1992  WIPO .

*Primary Examiner*—Carolyn Paden
*Attorney, Agent, or Firm*—Gerard J. McGowan, Jr.

[57] ABSTRACT

The invention concerns a process for the preparation of stanol fatty acid esters mixtures by interesterification of stanol fatty acid esters starting material, of which at least 50% of the fatty acid groups are saturated, with fatty acid mixtures containing at least 35%, and preferably at least 45%, of poly unsaturated fatty acid (PUFA) groups, and wherein preferably the hardening of sterol fatty acid esters. The sterol fatty acid esters are preferably prepared by the esterification of phytosterols with a fatty acid ester mixture comprising at least 70% of C18 fatty acids, all steps can be carried out in the absence of a solvent. Also claimed are food products comprising the stanol fatty acid esters obtained by the process.

15 Claims, No Drawings

PROCESS FOR THE PRODUCTION OF STANOL ESTERS, AND USE THEREOF

FIELD OF THE INVENTION

The present invention concerns a method for the production of stanol fatty acid esters, and the use of the thereby obtained stanol fatty acid ester products in food products, in particular in fat based food products in amounts sufficient to obtain a blood cholesterol lowering effect if the food product is used according to the common needs of the consumer.

BACKGROUND OF THE INVENTION

Fatty acid esters of phytosterols and/or phytostanols are hydrolysed in the gut and the subsequent free phytosterols and/or phytostanols will inhibit the absorption of cholesterol thereby lowering the blood cholesterol. Free phytosterols and/or phytostanols themselves are hardly absorbed. Indications in literature are that phytostanols are absorbed even in a lesser extend than phytosterols. The use of phytostanols in fat based food products to lower blood cholesterol could therefore be preferred over the use of phytosterols.

In U.S. Pat. No. 5,502,045 (Raision Tehtaat Oy AB) a substance of beta-sitostanol fatty acid ester is described produced by 1. solvent hardening of beta-sitosterol followed by 2. esterification of the formed beta-sitostanol with fatty acids. The so formed mixture of beta-sitostanol fatty acid esters can be used as such or added to a food.

There are several disadvantages to this production method, of which the most severe is that the beta-sitosterol should first be solubilized in a solvent (e.g. ethylacetate, butanol, ethanol) before the hardening of the sterol can be performed. Because the solubility of beta-sitosterol, or phytosterols in general, in solvents is rather limited, the hardening step is a relatively expensive operation because of high solvent costs and high costs of hardening equipment of relatively large volume. Moreover, the solvents need to be recovered after the hardening process is completed, and suitable locations for above hardening process will be limited because of environmental regulations. Furthermore, in a process aiming at the production of a food ingredient, removal of all solvents is essential, this making the process even more expensive.

SUMMARY OF THE INVENTION

In this invention, a process is proposed for the preparation of stanol fatty acid esters having any desired fatty acid groups, the preparation comprising the interesterification of stanol fatty acid esters with a source for one or more fatty acid moieties of a desired composition. Such a desired phytostanol fatty acid mixture can be obtained by interesterification with sources for fatty acid moieties containing high amounts (>35%, preferably >45%, more preferred >60%) of poly unsaturated fatty acid (PUFA) moieties. In a more preferred embodiment, a process for preparation of stanol fatty acid esters is proposed by the hardening of phytosterol fatty acid esters, followed by the interesterification of the so obtained stanol esters with sources for fatty acid moieties, preferably with the high PUFA fatty acid contents indicated above. By this method, stanol esters which will largely comprise saturated fatty acid groups, for example by hardening of phytosterol fatty acid esters, can be used to obtain a stanol ester mixture comprising fatty acid groups of a particularly desired composition. The use of a high PUFA mixture provides the additional advantage that it is considered that these stanol fatty acid esters have a very good solubility and blood cholesterol lowering efficacy in the body.

The process now proposed has the advantage over the process described in U.S. Pat. No. 5,502,045, that all steps in the preparation process, including the stanol hardening, can be carried out without the use of any solvent. The source of the fatty acid moieties that should be incorporated during the interestification suitably is a triglyceride, such as a natural, vegetable oil or free fatty acids. However other sources can be applied as well. In a further preferred process thereto, phytostanol fatty acid esters can by suitably prepared by the esterification of phytosterols, followed by hardening of the so formed phytosterol fatty acid esters, and subsequently interesterifying with a source for fatty acid moieties containing high amounts (>35%, preferably >45%, more preferred >60%) of poly unsaturated fatty acid (PUFA) groups.

Another advantage found with these preferred embodiments is that no solvents in the hardening step are needed since the phytosterol-esters are in a liquid form by themselves. Moreover, besides this method is solvent free and environmental friendly, and thus not requiring specific legal admissions, it is also more cost effective due to the fact that less raw materials, equipment and labour is required. Hence, a process in which all steps are carried out in full or substantial absence of a solvent can be achieved.

Preferably fatty acid mixtures of sunflower, safflower, rapeseed, linseed, linola and/or soybean are used as source for fatty acid moieties in the interesterification step. These are typical sources of high PUFA and/or low SAFA. Suitable interesterification conditions are described in the examples.

Where in this application sterols are mentioned, phytosterols (4-desmethylsterols, 4-monomethylsterols and 4,4'-dimethylsterols, and/or mixtures thereof) are meant. These sterols can be found as minor components in several plant materials. Sources are described in the literature. A preference for the use of vegetable sterols and/or stanols exists for this invention.

For obtaining the sterolesters before hardening is carried out, the sterols are esterified with one or more $C_{2-24}$ fatty acids. For the purpose of the invention the term $C_{2-24}$ fatty acid refers to any molecule comprising a $C_{2-24}$ main chain and at least one acid group. Although not preferred within the present context the $C_{2-24}$ main chain may be partially substituted or side chains may be present. Preferably, however the $C_{2-24}$ fatty acids are linear molecules comprising one or two acid group(s) as endgroup(s). Most preferred are linear $C_{8-22}$ fatty acids as occur in natural oils. Suitable esterification conditions are for example described in WO 92/19640.

Suitable examples of any such fatty acids are acetic acid, propionic acid, butyric acid, caproic acid, caprylic acid, capric acid. Other suitable acids are for example citric acid, lactic acid, oxalic acid and maleic acid. Preferred are lauric acid, palmitic acid, stearic acid, arachidic acid, behenic acid, oleic acid, cetoleic acid, erucic acid, elaidic acid, linoleic acid and linolenic acid.

Most preferred are the C18 polyunsaturated, monounsaturated or saturated fatty acids like stearic acid, oleic acid, elaidic, linoleic acid, alpha-linolenic acid and gamma-linolenic acid, since after fully hardening sterolesters comprising these fatty acids, the fatty acid part will be the saturated stearic acid, which has a neutral effect on blood cholesterol. Preferably, at least 60%, and more preferably at least 70% of the fatty acids are such C18 fatty acids.

When desired a mixture of fatty acids may be used. For example it is possible to use a natural occurring fat or oil as a source of the fatty acid and to carry out the esterification via an interesterification reaction. Most preferred are free fatty acid mixtures containing high amounts (>70%) of C18 polyunsaturated, monounsaturated or saturated fatty acids such as the free fatty acid mixtures of sunflower, safflower, rapeseed, linseed, linola and/or soybean.

Also subject of the invention are food products, in particular fat based food products, comprising the stanol (saturated) fatty acid ester (mixtures) in all embodiments set forth above. It is preferred that the food product comprises at least 1%, preferably at least 2%, and more preferably at least 5% stanol equivalents (present as stanol fatty acid esters). The use of these stanols in food products has the advantage that no regular intake of supplements is needed, and that through the normal food pattern, a significant reduction of the cholesterol level can be obtained. The use of the stanol esters of this invention is in particular preferred in fat based food products, this type of food products being part of the daily menu in most western world countries.

DETAILED DESCRIPTION OF THE INVENTION

Fat based food products are food products (partially) based on fat and regarded by the consumer, as 'fatty type of products'. Examples are yellow fat spreads (containing vegetable fat and/or animal fat such as butterfat), dressings, coffee-creamer, shortenings, cooking and frying oils, fillings and toppings, ice-cream and the like. These products in most cases comprise a particular amount of fat. In some cases, however, products are still regarded as 'fatty type of products', despite a replacement of part or even all the fat by fat replacers. Fat based food products in which the fat is partially or completely replaced by fat replacers are also covered by the term fat based food products of this invention.

The food products as such are common products in the western world, and are used by consumers on a daily basis in amounts different for each individual. The invention is in particular very suitable for yellow fat spreads, dressings, cheese, shortenings, cooking and frying oils and ice cream, with a preference for yellow fat spreads, mayonnaise, dressings, shortenings, cooking and frying oils. On the basis of habits of the consumer in the western world, the invention is preferred to concern particular for yellow fat spreads (including margarines, butter and low fat spreads) and dressings. Yellow fat spreads, for this invention, can comprise 0 (zero) to 90% fat (usually 5–80%). Dressings can comprise 0 to 85% fat (usually 5–80%), shortenings, cooking and frying oil more than 95% fat.

In such products, a further preference exists for the use of the stanol fatty acid esters of this invention in an amount of at least 3 wt % and more preferred of at least 5% wt. %, with a further preference for at least 7 wt % stanol equivalents (present as stanol fatty acid esters according to this invention).

The preparation of the fat based food products comprising the interesterified stanol fatty acid esters of the invention can be carried out in any suitable manner commonly known. Suitably, the stanol ester mixture can be added and dissolved to the fat prior to combining with the aqueous phase of the product to be prepared.

In a preferred embodiment, the food product is a yellow fat spread comprising 0 to 80% fat, at least 1 wt. % and preferably at least 2 wt. % and more preferably at least 5 wt % of stanol equivalents (present as interesterified stanol esters prepared according to the invention). In its most preferred embodiment, the amount of the stanol esters which are part of this invention is at least 5%, with optimal results found when the amount is in the range of 7–15%.

The invention is in particular suitable for low fat spreads having a fat level in the range of 0–40%, where the amount of cholesterol level reducing fat is low. However, another preference exists for higher fat level spreads (60–80% fat), as a very significant reduction of cholesterol level in the blood serum can be obtained when high PUFA fat level fats are used, and where the fat in the spread is not optimised on PUFA, to add the cholesterol lowering agent to such spreads.

The fat that is applied in these fat based food products can be any fat, such as dairy fat and/or vegetable fat. However, if fat is present, for health reasons the use of one or more vegetable fat sources is preferred. In particular, the use of liquid fats is preferred. The fat can be one single fat or a blend. The use of fat compositions comprising a considerable amount of PUFA rich triglycerides in addition to the use of the interesterified stanol fatty acid ester mixture is in particular considered as highly beneficial. For example, oils of sunflower, safflower, rapeseed, linseed, linola and/or soybean can be used in a preferred embodiment. Also the fat compositions mentioned in Netherlands patent documents no. NL 143115, NL 178559, Nl 155436, Nl 149687, Nl 155177, European patent documents EP 41303, EP 209176, EP 249282, and EP 470658 are highly suitable.

If a fat blend is used, it is preferred that it comprises at least 30%, and more preferred at least 45% of polyunsaturated fatty acids, based on the total weight amount of the fat in the fat based food product. So, a strong effect on the cholesterol lowering effect is obtained if use is made of the interesterified stanol fatty acid esters as set forth in this application in a food product in which a fat blend comprising at least 30 wt. % of PUFA rich triglycerides is used.

As fat spreads are a commonly and daily used product in western food eating habits, a preference exists for the use of a mixture of interesterified stanol fatty acid esters, in all the preferred embodiments as set forth above, in fat spreads.

Where butterfat is used for preparing spreads of the invention, or where the spreads are butter, it is preferred that the amount of interesterified stanol fatty acid esters is in the range of 5–15%, preferably 10–15%. As the consumption of butter is considered less beneficial for consumers health, the present invention is in particular suitable for making spreads containing butter or butter-melanges, as the negative effect associated with the butter consumption can be minimized or even reversed.

As by the additional step of interesterification of the stanol saturated fatty acid esters, as covered by this invention, the formed esters of phytostanol with saturated fatty acids are interesterified with sources for fatty acids moieties containing high amounts of PUFA, the remaining stanolesters mixtures comprising mainly polyunsaturated fatty acids will have less structuring properties than phytostanol with saturated fatty acids, due to their lower melting points. However, the amount of hardstock required to make a spreadable product out of liquid oils can be reduced compared to products without any form of stanolesters. This is in particular beneficial for the use of so prepared compositions in yellow fat spreads such as margarines, halvarines, low fat spreads, butter, and butter melanges comprising spreads.

EXAMPLES

Example 1a
Hydrogenation of steryl esters

A mixture of sterols derived from soybean oil distillates esterified with sunflowerseed oil fatty acids (to an esterification degree>85%) was hydrogenated on laboratory scale. As catalyst 5 wt % Pd on activated carbon was used. To 0.5 kg of the sterylesters 2 g of catalyst was added and the mixture was heated to 90 degrees C under reduced pressure 5–30 mbar.

The hydrogenation was carried out at 90 degrees C and at 3 bar hydrogen pressure. After 90 minutes approximately 40% of the theoretical amount of hydrogen was absorbed and again 2 g of catalyst was added. After 7.5 hours approx. 80% of the theoretical amount of hydrogen was absorbed and 2 g of catalyst was added and the temperature increased to 95–115 degrees C. Finally, after 11 hours of reaction approx. 100% of the theoretical amount of hydrogen was absorbed. At that moment no extra hydrogen was absorbed anymore and the hydrogenation was ended.

The major part of the catalyst was removed by filtration over a paper filter. The remaining part of the catalyst was removed by applying 2% Hyflow and filtration over a paper filter.

Analysis indicated that a hardening conversion of over 90% was achieved.

Example 1b
Interesterification of stanyl esters as prepared in Ex.1a (in SF-oil)

A mixture of mainly sitostanyl and campestanyl esters of stearate and palmitate fatty acids is interesterified with sunflowerseed oil.

1 kg stanylesters are mixed with 1 kg sunflowerseed oil in a reaction vessel and dried for 2 hours at 30 mbar and 125 degrees C. After cooling of the mixture to 110 degrees C the interesterification is started by adding 3 g of sodium methoxide catalyst. After 2 hours the mixture is cooled to 90 degrees C and the catalyst is destroyed by adding 200 g of water. After washing, the water is separated and the mixture is dried. Optionally, the mixture is bleached and deodorised.

Example 1c
Interesterification of stanyl esters as prepared in Ex.1a (with SF-FAME).

A mixture of mainly sitostanyl and campestanyl esters of stearate and palmitate fatty acids is interesterified with methylesters prepared from sunflowerseed oil.

1 kg stanylesters are mixed with 1 kg methylesters prepared from sunflowerseed oil and dried for 2 hours at 30 mbar and 125 degrees C. After cooling of the mixture to 110 degrees C the interesterification is started by adding 3 g of sodium methoxide catalyst. After 2 hours the mixture is cooled to 90 degrees C and the catalyst is destroyed by adding 200 g of water. After washing, the water is separated and the mixture is dried and bleached. The residual methylesters are removed by stripping/deodorisation.

Example 2a
Preparation of a spread 70% fat (Stanol esters Ex.1a)

Refined sunflower oil (65% PUFA as linoleic acid) was enriched with esterified stanols as obtained from Example 1a (to a total stanol equivalent concentration of 45%). Of this stanol-ester concentrate, 22 parts were mixed with 35 parts of normal refined sunflower oil, 15 parts of refined rapeseed oil and 8 parts of a refined interesterified mixture of 65 parts fully hardened palm oil and 35 parts fully hardened palm kernel oil. To this fatblend, small amounts of soybean lecithin, monoglyceride, flavours and beta-carotene solution were added.

To 18 parts water, small amounts of whey protein powder, flavour, and citric acid were added to obtain a pH of 4.8.

80 parts of the fat phase composition (containing 70% of fat) and 20 parts of the aqueous phase composition were mixed and kept at 60 degrees C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11 degrees C. It was filled into tubs and stored at 5 degrees C. A good and stable, high PUFA, high fat-continuous spread enriched with 10% stanol equivalents (mainly present as C18:0 stanol esters) was obtained.

Example 2b
Preparation of a spread 70% fat (Interesterify Ex.1b)

Refined sunflower oil (65% PUFA as linoleic acid) was enriched with esterified stanols as obtained from Example 1b (to a total stanol equivalent concentration of 30%). Of this stanol-ester concentrate, 33 parts were mixed with 21 parts of normal refined sunflower oil, 15 parts of refined rapeseed oil and 11 parts of a refined interesterified mixture of 65 parts fully hardened palm oil and 35 parts fully hardened palm kernel oil. To this fatblend, small amounts of soybean lecithin, monoglyceride, flavours and beta-carotene solution were added.

To 18 parts water, small amounts of whey protein powder, flavour, and citric acid were added to obtain a pH of 4.8.

80 parts of the fat phase composition (containing 70% of fat) and 20 parts of the aqueous phase composition were mixed and kept at 60 degrees C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11 degrees C. It was filled into tubs and stored at 5 degrees C. A good and stable, high PUFA, high fat-continuous spread enriched with 10% stanol equivalents (mainly present as C18:2 stanol esters) was obtained.

Example 3a
Preparation of a spread 40% (Stanol esters Ex.1a)

Refined sunflower oil (65% PUFA as linoleic acid) was enriched with esterified stanols as obtained from Example 1a (to a total stanol equivalent concentration of 45%). Of this stanol-ester concentrate, 22 parts were mixed with 23 parts of normal refined sunflower oil and with 5 parts of a refined interesterified mixture of 50 parts fully hardened palm oil and 50 parts fully hardened palm kernel oil. To this fatblend small amounts of soybean lecithin, monoglyceride and beta-carotene solution were added.

To 44 parts water, gelatin and small amounts of whey protein powder, flavours, preservative and citric acid were added to obtain a pH of 4.7.

50 parts of the fat phase composition (containing 40% of fat) and 48 parts of the aqueous phase composition were mixed and kept at 60 degrees C. The mixture was then passed through a Votator line with 2 scraped surface heat exchangers (A-units) and 2 stirred crystallizers (C-unit), in ACAC-sequence operating at 500, 1000, 600 and 100 rpm respectively. The product leaving the last C-unit had a temperature of 10 degrees C. It was filled into tubs and stored at 5 degrees C. A good and stable, high PUFA, low fat-continuous spread enriched with 10% stanol equivalents (mainly present as C18:0 stanol esters) was obtained.

Example 3b

Preparation of a spread 40% (Interesterified Ex.1c)

Refined sunflower oil (65% PUFA as linoleic acid) was enriched with esterified stanols as obtained from Example 1a (to a total stanol equivalent concentration of 30%). Of this stanol-ester concentrate, 33 parts were mixed with 11 parts of normal refined sunflower oil and with 6 parts of a refined interesterified mixture of 50 parts fully hardened palm oil and 50 parts fully hardened palm kernel oil. To this fatblend small amounts of soybean lecithin, monoglyceride and beta-carotene solution were added.

To 44 parts water, gelatin and small amounts of whey protein powder, flavours, preservative and citric acid were added to obtain a pH of 4.7.

50 parts of the fat phase composition (containing 40% of fat) and 48 parts of the aqueous phase composition were mixed and kept at 60 degrees C. The mixture was then passed through a Votator line with 2 scraped surface heat exchangers (A-units) and 2 stirred crystallizers (C-unit), in ACAC-sequence operating at 500, 1000, 600 and 100 rpm respectively. The product leaving the last C-unit had a temperature of 10 degrees C. It was filled into tubs and stored at 5 degrees C. A good and stable, high PUFA, low fat-continuous spread enriched with 10% stanol equivalents (mainly present as C18:2 stanol esters) was obtained.

Example 4a

Preparation of a dressing (Stanol esters Ex.1a)

49 parts of water is mixed with 11 parts of various flavour components, preservatives, thickeners and emulsifiers. The mixture is thoroughly mixed in a stainless steel stirred vessel. To this aqueous mixture 20 parts of sunflower oil (65% PUFA as linoleic acid) enriched with 40% stanol equivalents present as stanol esters as obtained from Example 1a is added. To above oil in water mixture, 20 parts of normal refined sunflower oil is added, thoroughly mixed for an additional 15 min, to obtain a pre-emulsion. The pre-emulsion is brought into a colloid mill (Prestomill PM30) and processed at a split-size between level 15 and 20 and a throughput between level 4 and 6. A good and stable water continuous dressing enriched with 8% stanol equivalents (mainly present as C18:0 stanol esters) is obtained.

What is claimed is:

1. Process for the preparation of stanol fatty acid esters mixtures comprising interesterifying stanol fatty acid esters starting material, of which at least 50% of the fatty acid groups are saturated, with a source for one or more fatty acid moieties containing at least 35% of poly unsaturated fatty acid (PUFA) groups.

2. Process according to claim 1, characterised in that the source for fatty acid moieties comprises at least 60% PUFA.

3. Process according to claim 1, characterised in that the stanol fatty acid ester starting material is prepared by the hardening of sterol fatty acid esters.

4. Process according to claim 3, wherein the sterol fatty acid esters is prepared by the esterification of phytosterols with a source for fatty acid moieties comprising at least 70% of C18 fatty acids.

5. Process according to claim 1, wherein any of the steps in the preparation is carried out in the substantial absence of a solvent.

6. Food product comprising a stanol fatty acid ester mixture prepared by a process according to claim 1.

7. Food product according to claim 6, wherein at least 1%, stanol equivalents are present (as stanol fatty acid ester mixture).

8. The food product according to claim 7, wherein at least 2% stanol equivalents are present.

9. The food product according to claim 8 wherein at least 5% stanol equivalents are present.

10. Food product according to claim 6, wherein the food product is a fat based food product.

11. Food product according to claim 10, wherein the food product is a yellow fat spread comprising 0–80% fat.

12. The food product according to claim 11 which comprises at least 5% stanol equivalents.

13. Food product according to claim 10, wherein the fat or fat blend used in the product comprises at least 30 wt % of PUFA rich triglycerides, calculated on the total weight of the fat present in the product.

14. The food product according to claim 13 wherein the fat or fat blend comprises at least 45 wt % PUFA rich triglycerides.

15. The process according to claim 1 wherein the source of fatty acid moieties contains at least 45% PUFA groups.

* * * * *